(12) United States Patent
Sakaguchi et al.

(10) Patent No.: US 9,949,698 B2
(45) Date of Patent: *Apr. 24, 2018

(54) X-RAY IMAGING APPARATUS, MEDICAL IMAGE PROCESSING APPARATUS, X-RAY IMAGING METHOD AND MEDICAL IMAGE PROCESSING METHOD

(71) Applicant: Toshiba Medical Systems Corporation, Otawara-shi (JP)

(72) Inventors: Takuya Sakaguchi, Utsunomiya (JP); Hisato Takemoto, Amherst, MA (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 29 days.

This patent is subject to a terminal disclaimer.

(21) Appl. No.: 14/218,436

(22) Filed: Mar. 18, 2014

(65) Prior Publication Data

US 2014/0198897 A1 Jul. 17, 2014

Related U.S. Application Data

(63) Continuation of application No. PCT/JP2013/060706, filed on Apr. 9, 2013.

(30) Foreign Application Priority Data

May 9, 2012 (JP) ................... 2012-107934

(51) Int. Cl.
*A61B 6/02* (2006.01)
*A61B 6/00* (2006.01)

(52) U.S. Cl.
CPC ............ *A61B 6/022* (2013.01); *A61B 6/4441* (2013.01); *A61B 6/502* (2013.01); *A61B 6/466* (2013.01)

(58) Field of Classification Search
CPC .. A61B 6/5205; A61N 5/1031; A61N 5/1067; A61N 5/1071
See application file for complete search history.

(56) References Cited

U.S. PATENT DOCUMENTS

| | | | | |
|---|---|---|---|---|
| 5,034,987 A | * | 7/1991 | Fujimoto | A61B 6/463 |
| | | | | 382/131 |
| 5,090,038 A | * | 2/1992 | Asahina | A61B 6/022 |
| | | | | 348/E13.001 |

(Continued)

FOREIGN PATENT DOCUMENTS

| CN | 1215315 A | 4/1999 |
|---|---|---|
| CN | 102204825 A | 10/2011 |

(Continued)

OTHER PUBLICATIONS

International Preliminary Report on Patentability and Written Opinion dated Nov. 20, 2014, in PCT/JP2013/060706 filed Apr. 9, 2013.

(Continued)

*Primary Examiner* — Glen Kao
(74) *Attorney, Agent, or Firm* — Oblon, McClelland, Maier & Neustadt, L.L.P.

(57) ABSTRACT

According to one embodiment, an X-ray imaging apparatus includes an X-ray imaging system, a control system, and a display processing circuit. The X-ray imaging system is configured to acquire X-ray image data of an object. The control system is configured to control the imaging system to acquire frames of X-ray image data corresponding to mutually different not less than three directions by reciprocating the imaging system. The display processing circuit is configured to generate stereoscopically visible image data by lining up the frames of the X-ray image data in a display order different from an acquisition order of the frames of the (Continued)

| TIME | T1 | T2 | T3 | T4 | T5 | T6 | T7 | T8 | T9 | T10 | T11 | T12 | T13 |
|---|---|---|---|---|---|---|---|---|---|---|---|---|---|
| ACQUIRED IMAGE | D1 | D2 | D3 | D4 | D5 | D6 | D7 | D8 | D9 | D10 | D11 | D12 | D13 |
| DISPLAYED IMAGE FOR LEFT EYE | | D1 | D2 | D3 | D4 | D6 | D7 | D8 | D9 | D9 | D10 | D11 | D12 |
| DISPLAYED IMAGE FOR RIGHT EYE | | D2 | D3 | D4 | D5 | D5 | D6 | D7 | D8 | D10 | D11 | D12 | D13 |
| ACQUIRED POSITION | RAO | → | | LAO | | → | | RAO | | → | | LAO | |
| OPERATING STATE | STOP | MOVE | | STOP | | MOVE | | STOP | | MOVE | | STOP | |

→ TIME

X-ray image data. The display order is according to a moving direction of the imaging system.

17 Claims, 8 Drawing Sheets

(56) References Cited

U.S. PATENT DOCUMENTS

| | | | | |
|---|---|---|---|---|
| 5,448,610 | A * | 9/1995 | Yamamoto | A61B 6/022 348/E13.005 |
| 5,825,997 | A * | 10/1998 | Yamada | H04N 13/0055 345/419 |
| 9,480,438 | B2 * | 11/2016 | Sakaguchi | A61B 6/486 |
| 2011/0235776 | A1 * | 9/2011 | Kusunoki | H04N 13/0221 378/37 |

FOREIGN PATENT DOCUMENTS

| | | |
|---|---|---|
| JP | 4-166135 A | 6/1992 |
| JP | 2006-136741 A | 6/2006 |
| JP | 2009-017322 A | 1/2009 |
| JP | 2011-200408 A | 10/2011 |
| JP | 2011-206206 A | 10/2011 |
| WO | WO98/24368 A2 | 6/1998 |

OTHER PUBLICATIONS

International Search Report dated Jul. 16, 2013 for PCT/JP2013/060706 filed Apr. 9, 2013 with English Translation of Categories.
International Written Opinion dated Jul. 16, 2013 for PCT/JP2013/060706 filed Apr. 9, 2013.
Combined Office Action and Search Report dated Feb. 3, 2015 in Chinese Patent Application No. 201380000747.0 (with English Translation of Category of Cited Documents).
Combined Chinese Office Action and Search Report dated Dec. 7, 2015 in Patent Application No. 201380000747.0 (with English translation of Categories of Cited Documents).
Japanese Office Action dated Mar. 8, 2016 in Patent Application No. 2012-107934.

* cited by examiner

| TIME | T1 | T2 | T3 | T4 | T5 | T6 | T7 | T8 | T9 | T10 | T11 | T12 | T13 |
|---|---|---|---|---|---|---|---|---|---|---|---|---|---|
| ACQUIRED IMAGE | D1 | D2 | D3 | D4 | D5 | D6 | D7 | D8 | D9 | D10 | D11 | D12 | D13 |
| DISPLAYED IMAGE FOR LEFT EYE | | D1 | D2 | D3 | D4 | D6 | D7 | D8 | D9 | D9 | D10 | D11 | D12 |
| DISPLAYED IMAGE FOR RIGHT EYE | | D2 | D3 | D4 | D5 | D5 | D6 | D7 | D8 | D10 | D11 | D12 | D13 |
| ACQUIRED POSITION | RAO | → | | LAO | | → | | RAO | | → | | LAO |
| OPERATING STATE | STOP | MOVE | | STOP | | MOVE | | STOP | | MOVE | | STOP |

→ TIME

X-RAY IMAGING APPARATUS, MEDICAL IMAGE PROCESSING APPARATUS, X-RAY IMAGING METHOD AND MEDICAL IMAGE PROCESSING METHOD

CROSS REFERENCES TO RELATED APPLICATIONS

This is a continuation of Application PCT/JP2013/60706, filed Apr. 9, 2013.

This application is based upon and claims the benefit of priority from Japanese Patent Application No. 2012-107934, filed May 9, 2012; the entire contents of which are incorporated herein by reference.

FIELD

Embodiments described herein relate generally to an X-ray imaging apparatus, a medical image processing apparatus, an X-ray imaging method and a medical image processing method.

BACKGROUND

Conventionally, a technology for displaying X-ray diagnostic images which allow stereoscopically viewing an imaging target, such as a blood vessel, using an X-ray imaging apparatus has been proposed. Assuming that images which allow stereoscopic viewing of an imaging target are referred to as 3D (three dimensional) images, it is necessary to make an image for left eye and an image for right eye visible individually by the left eye and the right eye respectively in order to display one frame of 3D image.

Examples of method of respectively acquiring images for left eye and right eye using an X-ray imaging apparatus include a method of respectively acquiring 2D (two dimensional) X-ray projection images for left eye and right eye actually besides a method by image reconstruction processing. The X-ray projection images for left eye and right eye can be also acquired by an X-ray imaging apparatus having a single X-ray imaging system as well as an X-ray imaging apparatus having plural X-ray imaging systems.

In case of using an X-ray imaging apparatus having a single X-ray imaging system, the X-ray imaging system is positioned to the first position by moving the C-shaped arm of the X-ray imaging apparatus. Then, an X-ray projection image for left eye corresponding to the first position can be acquired with stopping the X-ray imaging system. Next, the C-shaped arm of the X-ray imaging apparatus are moved to position the X-ray imaging system to the second position. Then, an X-ray projection image for right eye corresponding to the second position can be acquired with stopping the X-ray imaging system. Alternatively, the X-ray projection images for left eye may be acquired after acquiring the X-ray projection images for right eye.

On the other hand, X-ray projection images for left eye and right eye can be acquired using an X-ray imaging apparatus having two X-ray imaging systems. In this case, the X-ray projection images for left eye and right eye can be acquired at a same timing by positioning the two X-ray imaging systems appropriately.

The X-ray projection images for left eye and right eye acquired as described above can be used as two-parallax images for displaying a 3D image. As a method of displaying one set of two-parallax images as a 3D image allowing stereoscopic viewing, a method of displaying images for left eye and right eye alternately with a time division so as to be viewed through a dedicated glasses, a method of displaying images for left eye and right eye on a dedicated display without using a glasses, and the like are known.

Especially, acquiring X-ray projection images for left eye and right eye at a same timing using an X-ray imaging apparatus having two X-ray imaging systems makes it possible to display a 3D image, having an improved image quality, less influenced by a motion of an object.

Furthermore, generating two-parallax images by image reconstruction processing makes it possible to display 3D images allowing stereoscopic viewing from various observation directions.

PRIOR TECHNICAL LITERATURE

[Patent literature 1] JPA H104-166135

However, there is a problem that the X-ray imaging apparatus having plural X-ray imaging systems has a complex structure and is expensive. Moreover, when a 3D image for stereoscopic viewing is generated by image reconstruction processing, there is a problem that a data processing amount becomes huge and a data processing time also becomes long.

Accordingly, an object of the present invention is to provide an X-ray imaging apparatus, a medical image processing apparatus, an X-ray imaging method and a medical image processing method by which X-ray images useful for a diagnosis can be displayed as a 3D image for stereoscopic viewing with a simpler and more inexpensive structure.

DETAILED DESCRIPTION

In general, according to one embodiment, an X-ray imaging apparatus includes an X-ray image acquisition unit, a control system and a display processing part. The X-ray image acquisition unit is configured to acquire X-ray image data of an object by using at least one imaging system. The control system is configured to control the imaging system to acquire frames of X-ray image data corresponding to mutually different not less than three directions by reciprocating the imaging system. The display processing part is configured to generate stereoscopically visible image data with lining up the frames of the X-ray image data in a display order different from an acquisition order of the frames of the X-ray image data. The display order is according to a moving direction of the imaging system.

Further, according to another embodiment, a medical image processing apparatus includes an image acquisition part and a display processing part. The image acquisition part is configured to acquire frames of X-ray image data corresponding to mutually different not less than three directions. The frames of the X-ray image data are acquired by reciprocating a single imaging system. The display processing part is configured to generate stereoscopically visible image data with lining up the frames of the X-ray image data in a display order different from an acquisition order of the frames of the X-ray image data. The display order is according to a moving direction of the imaging system.

Further, according to another embodiment, an X-ray imaging method includes: acquiring X-ray image data of an object by using at least one imaging system; controlling the imaging system to acquire frames of X-ray image data corresponding to mutually different not less than three directions by reciprocating the imaging system; and generating stereoscopically visible image data with lining up the frames of the X-ray image data in a display order different from an acquisition order of the frames of the X-ray image data. The display order is according to a moving direction of the imaging system.

Further, according to another embodiment, a medical image processing method includes: acquiring frames of X-ray image data corresponding to mutually different not less than three directions; and generating stereoscopically visible image data with lining up the frames of the X-ray image data in a display order different from an acquisition order of the frames of the X-ray image data. The frames of the X-ray image data are acquired by reciprocating a single imaging system. The display order is according to a moving direction of the imaging system.

An X-ray imaging apparatus, a medical image processing apparatus, an X-ray imaging method and a medical image processing method according to embodiments of the present invention will be described with reference to the accompanying drawings.

Figure 1:
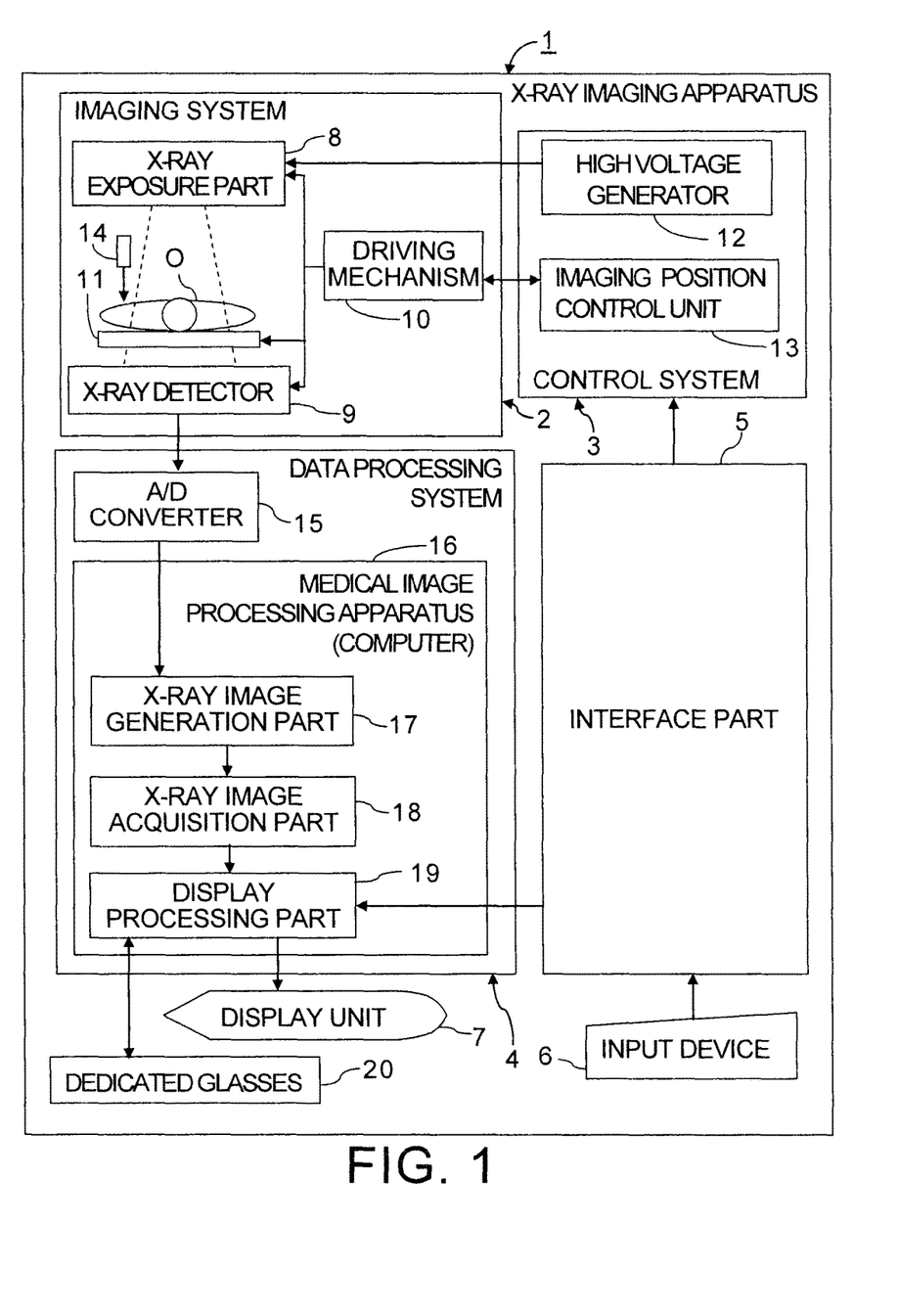
FIG. 1 is a configuration diagram of an X-ray imaging apparatus and a medical image processing apparatus according to one embodiment of the present invention.

FIG. 1 is a configuration diagram of an X-ray imaging apparatus and a medical image processing apparatus according to one embodiment of the present invention.

An X-ray imaging apparatus 1 includes an imaging system 2, a control system 3, and a data processing system 4, an interface part 5, an input device 6 and a display unit 7. The imaging system 2 has an X-ray exposure part 8, an X-ray detector 9, a driving mechanism 10 and a bed 11. The control system 3 has a high voltage generator 12 and an imaging position control unit 13.

The X-ray exposure part 8 includes an X-ray tube and is placed in the opposite side of the X-ray detector 9 so that an object O set on the bed 11 lies between the X-ray exposure part 8 and the X-ray detector 9. The X-ray exposure part 8 and the X-ray detector 9 can change the angle and the relative position with respect to the object O with keeping their relative position by driving the driving mechanism 10. Specifically, the X-ray exposure part 8 and the X-ray detector 9 are settled at both ends of the C-shaped arm having the rotational function. Then, the X-ray exposure part 8 is configured to expose an X-ray from a predetermined angle to an object O by the X-ray tube to detect the X-ray having transmitted the object O by the X-ray detector 9.

Moreover, the incline and the position of the table of the bed 11 can be adjusted with the driving mechanism 10. Therefore, the radiation direction of an X-ray toward an object O can be changed by adjusting not only the angle of the X-ray exposure part 8 and the X-ray detector 9 with regard to the object O but also the angle of the table.

Furthermore, a contrast medium injector 14 is provided in the vicinity of the object O set on the bed 11 in order to inject a contrast agent into the object O, as needed.

The high voltage generator 12 of the control system 3 is a unit which applies a high voltage to the X-ray tube of the X-ray exposure part 8 to expose an X-ray, having a desired energy, toward the object O. The imaging position control unit 13 is a unit which outputs a control signal to the driving mechanism 10 to control the driving mechanism 10. That is, the inclination and position of the top plate of the bed 11, and the rotation angle and position of the X-ray exposure part 8 and the X-ray detector 9 are controlled by the control signal output to the driving mechanism 10 from the imaging position control unit 13.

The data processing system 4 has an A/D (analog to digital) converter 15 and a computer 16. The computer 16 functions as a medical image processing apparatus 16 by executing programs. That is, the medical image processing apparatus 16 is built in the X-ray imaging apparatus 1.

However, an independent medical image processing apparatus having the similar function may be connected to the X-ray imaging apparatus 1 through a network. Moreover, circuits may be used for configuring the medical image processing apparatus 16 built in the X-ray imaging apparatus 1 or the medical image processing apparatus connected with the X-ray imaging apparatus 1 through a network. Meanwhile, the computer 16 may function as the interface part 5.

The medical image processing apparatus 16 has an X-ray image generation part 17, an X-ray image acquisition part 18 and a display processing part 19. The X-ray image generation part 17 has a function to read digitized X-ray detection data from the X-ray detector 9 through the A/D converter 15 to generate X-ray image data by data processing of the read X-ray detection data.

Therefore, the X-ray imaging apparatus 1 has a function as an X-ray image acquisition unit, which acquires X-ray image data of an object O using the imaging system 2, by collaboration of the X-ray image generation part 17 with the imaging system 2 and the control system 3.

The X-ray image acquisition part 18 has a function to acquire the X-ray image data generated in the X-ray image generation part 17 and give the X-ray image data to the display processing part 19. Especially, in an independent medical image processing apparatus connected to the X-ray imaging apparatus 1 through a network, the X-ray image generation part 17 can be omitted. In this case, a function to acquire the X-ray image data from the X-ray image generation part 17 included in the X-ray imaging apparatus 1 through a network is provided with the X-ray image acquisition part 18.

The display processing part 19 has a function to acquire frames of X-ray image data including a frame of X-ray image data for left eye and a frame of X-ray image data for right eye from the X-ray image acquisition part 18; a function to generate 3D image data, as image data allowing stereoscopic viewing, based on the acquired frames of the X-ray image data; and a function to display the generated 3D image data on the display unit 7.

As a method of displaying a 3D image for stereoscopic viewing based on frames of X-ray image data for left eye and right eye, an arbitrary known method can be used. As typical methods, a method by using an usual display and a dedicated glasses and a method by using a dedicated display are known.

In case of using a dedicated glasses, a method of alternately indicating images for left eye and images for right eye with a constant temporal difference and preparing a function as a polarization plate with the dedicated glasses is known. In this case, circular polarized lights in mutually different rotational directions are given to the images for left eye and right eye. Thus, using a circular light glasses makes two-parallax images visible individually by the left and right eyes.

Alternatively, a method of indicating an image for left eye and an image for right eye as images in mutually different bands of wavelength with a time division is also known. In this case, the image for left eye and the image for right eye, which have transmitted a filter to become lights in the mutually different bands of wavelength, are visually recognized by the left and right eyes individually through a wavelength selection glasses.

Furthermore, another method for indicating images for left eye and images for right eye alternately with a time division so that the images for left eye and the images for right eye can be visually recognized with a glasses whose shutters for left eye and right eye open and close in synchronized with the time division is also known.

Conversely, a method for outputting positional information and directional information from a dedicated glasses and changing images to be output on a display according to the positional information and the directional information of the glasses is also known.

On the other hand, as a method without using a dedicated glasses, a method of overlapping a wave plate, having a phase difference, on the surface of a display, a method of overlapping a film, on which a convexoconcave having lines per inch different from a resolution of a display is arranged, on the surface of the display, and the like are known. Each of these methods is also called a spatial division method by which images for left eye and images for right eye are visually recognized by the left and right eyes respectively through a wave plate or a film.

Therefore, the X-ray imaging apparatus 1 has elements according to a displaying method of a 3D image. For example, a dedicated glasses 20 is connected with the computer 16 when it is required for the 3D display. Moreover, a dedicated display for 3D display is connected as the display unit 7 with the computer 16 when it is required for the 3D display. Thus, the display processing part 19 is configured to output and input information required for 3D display to one or both of the display unit 7 and the glasses 20.

On the other hand, the control system 3 has a function to control the single imaging system 2 in order to acquire frames of X-ray image data for left eye and right eye required for stereoscopic viewing. Specifically, the control system 3 has a function to control the imaging system 2 so that frames of X-ray image data corresponding to mutually different directions are acquired by reciprocating the imaging system 2 like a pendulum. Then, the control system 3 is configured to variably control a moving range of the imaging system 2 and exposure timings or exposure positions of X-rays arbitrarily.

Then, the display processing part 19 is configured to generate X-ray image data for 3D display by display processing according to acquisition positions of frames of X-ray image data, having two or more parallaxes, acquired with moving the single imaging system 2. Specifically, using two frames of X-ray image data, corresponding to mutually different two directions, as two-parallax image data can generate one frame of image data which can be stereoscopically viewed from one direction. Alternatively, stereoscopic image data whose hue changes according to viewing directions, i.e., image data which can be stereoscopically viewed from mutually different directions can be generated based on frames of X-ray image data corresponding to three or more different directions.

Figure 2:
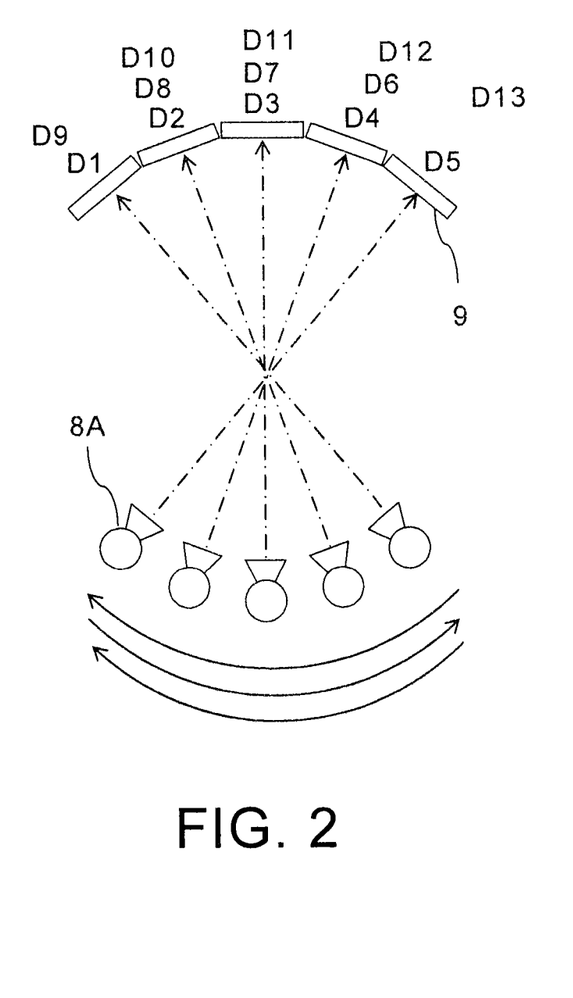
FIG. 2 shows a control method of the imaging system by the control system shown in FIG. 1.

FIG. 2 shows a control method of the imaging system 2 by the control system 3 shown in FIG. 1.

As shown in FIG. 2, the X-ray tube 8A of the X-ray exposure part 8 and X-ray detector 9 can be reciprocated like a pendulum so that frames of X-ray image data corresponding to three or more different directions are acquired in each of the outward way and the return way. In this case, at least one of the frames of the X-ray image data is to be acquired during the movement of the imaging system 2.

Moreover, frames of X-ray image data, corresponding to a same direction, whose number depends on the number of the reciprocations of the X-ray detector 9 and the X-ray tube 8A are acquired. For example, if the X-ray tube 8A and the X-ray detector 9 turn back twice and acquire data at five positions as shown in FIG. 2, thirteen frames of X-ray image data D1, D2, D3, . . . , D13 are acquired sequentially. Therefore, two frames of X-ray image data correspond to each of the both ends of the moving range of the imaging system 2 while three frames of X-ray image data correspond to each of the other positions of the imaging system 2.

However, no frames of X-ray image data may be acquired at the both ends of the moving range of the imaging system 2. In that case, the same numbers of frames of X-ray image data are acquired at each position during the movement of the imaging system 2.

When the imaging system 2 is controlled by the control system 3 as shown in FIG. 2, frames of X-ray image data, corresponding to mutually different three or more directions, acquired by reciprocating the single imaging system 2 are acquired in the image acquisition part 18. For this reason, the display processing part 19 can generate 3D image data allowing stereoscopic viewing based on the frames of the X-ray image data corresponding to the three or more different directions.

Figure 3:
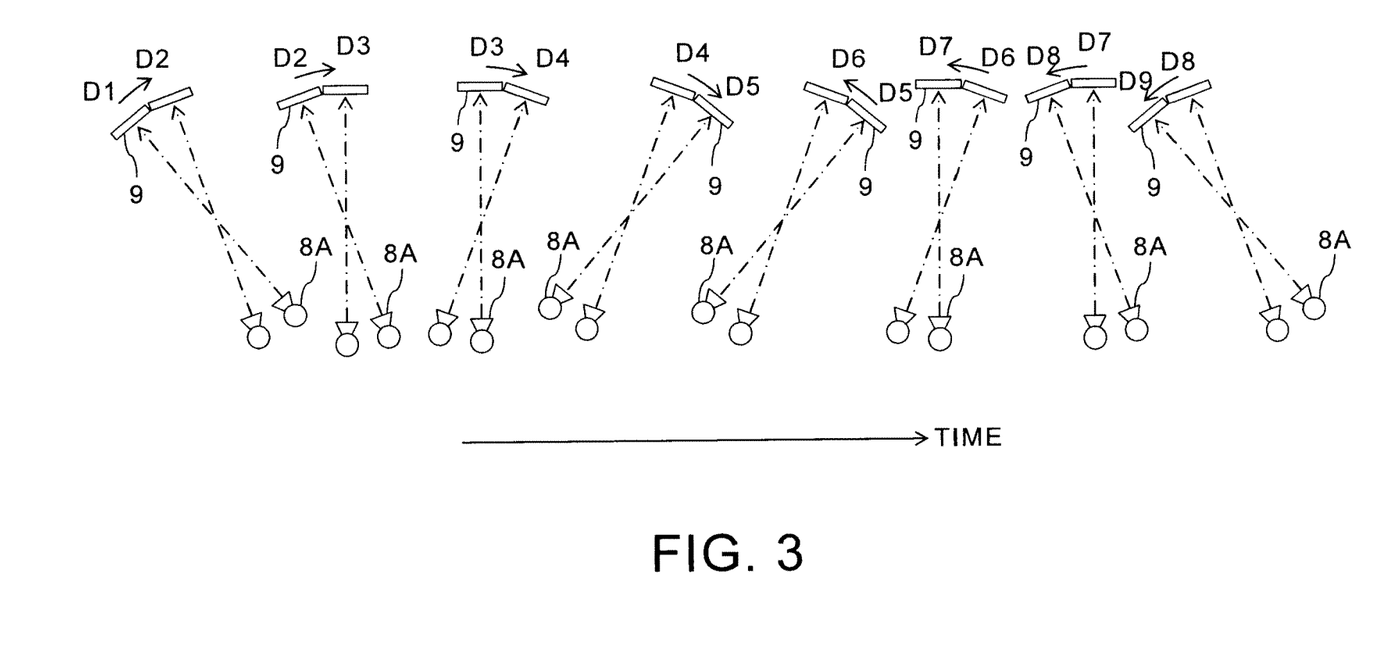
FIG. 3 is a view for explaining a method of display processing in the display processing part shown in FIG. 1.

FIG. 3 is a view for explaining a method of display processing in the display processing part 19 shown in FIG. 1.

In FIG. 3, the horizontal axis direction represents time. Moreover, the respective positions of the X-ray tube 8A and the X-ray detector 9 shown in FIG. 3 represent acquisition positions of frames of X-ray image data displayed as one frame of stereoscopic image.

As shown in FIG. 3, frames of image data, which can be stereoscopically viewed from mutually different directions, can be generated by sequentially generating one frame of image data, allowing stereoscopic viewing, based on two frames of X-ray image data corresponding to two different directions. That is, the imaging system 2 can be reciprocated continuously and a newly acquired image and an image acquired in the past can be indicated and updated as a pair of two-parallax images.

When the display control of stereoscopic images as shown in FIG. 3 is performed, one of images which constitute a stereoscopic image is updated and the pair of two-parallax images changes whenever a new image is acquired. Therefore, the stereoscopic images serve as a moving image to which the viewpoint changes sequentially. Accordingly, an imaged target is to be seen with a rotation.

However, if the two frames of the X-ray image data are displayed sequentially, as they are, in the order for acquisition of the frames of the X-ray image data as shown in FIG. 3, the spatial relationship in the depth direction changes periodically due to the inversion of the moving direction of the imaging system 2.

Accordingly, the display processing part 19 is configured to generate stereoscopically visible image data with lining up the frames of the X-ray image data in a display order different from the acquisition order of the frames of the X-ray image data, according to the moving direction and the rotational direction of the imaging system 2.

Figure 4:
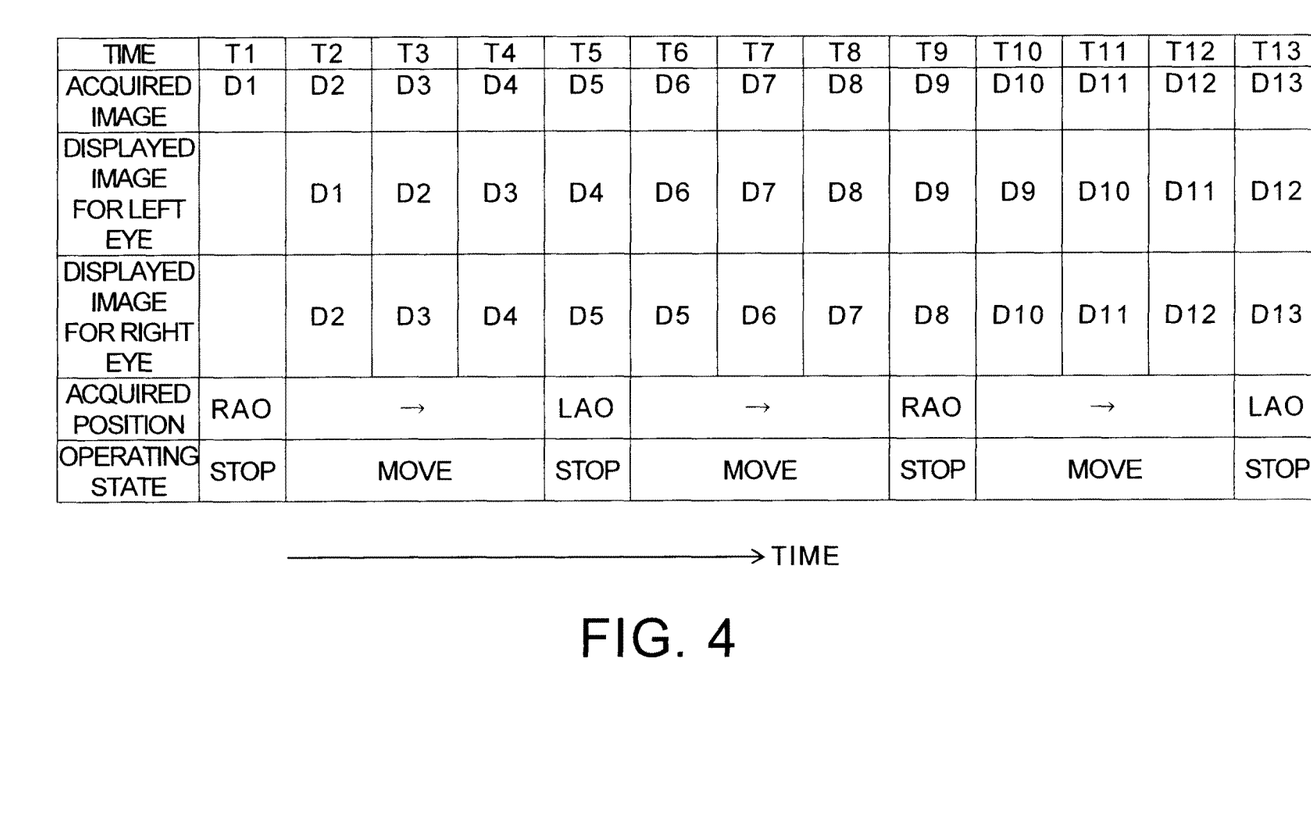
FIG. 4 is a table for explaining a method of reordering processing of the display order for X-ray images in the display processing part shown in FIG. 1.

FIG. 4 is a table for explaining a method of reordering processing of the display order for X-ray images in the display processing part 19 shown in FIG. 1.

In FIG. 4, the horizontal axis direction represents time. As shown in FIG. 4, frames of X-ray image data D1, D2, D3, . . . , D13 are sequentially acquired at the respective times T1, T2, T3, . . . , T13. More specifically, an X-ray is exposed from a RAO (right anterior oblique) direction at the time T1 in the state that the imaging system 2 is static. Thereby, the frame of the X-ray image data D1 is acquired.

Next, the imaging system 2 moves toward a LAO (left anterior oblique) direction from a RAO direction and the frames of the X-ray image data D2, D3, and D4 corresponding to the times T2, T3, and T4 are acquired sequentially in the state that the imaging system 2 are moving. Then, an X-ray is exposed from an LAO direction at the time T5 in the state that the imaging system 2 is static. Thereby, the frame of the X-ray image data D5 is acquired.

Next, the imaging system 2 reverses to move toward an RAO direction from an LAO direction. Then, the frames of the X-ray image data D6, D7, and D8 corresponding to the times T6, T7, and T8 are acquired sequentially in the state that the imaging system 2 are moving. After that, an X-ray is exposed from an RAO direction at the time T9 in the state that the imaging system 2 is static. Thereby, the frame of the X-ray image data D9 is acquired.

Next, the imaging system 2 reverses again to move toward an LAO direction from an RAO direction. Then, the frames of the X-ray image data D10, D11, and D12 corresponding to the time T10, T11, and T12 acquired sequentially in the state that the imaging system 2 are moving. Furthermore, an X-ray is exposed from an LAO direction at the last time T13 in the state that the imaging system 2 is static. Thereby, the frame of the X-ray image data D13 is acquired.

Thus, the frames of the X-ray image data D1, D2, D3, . . . , D13 in the time series can be acquired by reciprocating the imaging system 2. However, the positions of the frames of the X-ray image data D1, D2, D3, . . . , D13 reverse if the frames of the X-ray image data D1, D2, D3, . . . , D13 are aligned in the acquisition order. Therefore, displaying the frames of the X-ray image data D1, D2, D3, . . . , D13 in the acquisition order, as stereoscopic images, results in a change in the positional relationship in the depth direction Accordingly, the frames of the X-ray image data D1, D2, D3, . . . , D13 acquired in the time series are permutated according to the moving direction of the imaging system 2.

Specifically, the display processing part 19 performs reordering processing of frames of image data so that the newest frame of X-ray image data acquired in the state that the imaging system 2 were moving to an LAO direction from an RAO direction is used for the right eye while the newest frame of X-ray image data acquired in the state that the imaging system 2 were moving to an RAO direction from an LAO direction is used for the left eye. That is, when the newest frame of X-ray image data has been acquired for the duration of a movement of the imaging system 2 to an LAO direction from an RAO direction, the newest frame of the X-ray image data can be used for the right eye. On the other hand, when the newest frame of X-ray image data has been acquired for the duration of a movement of the imaging system 2 to an RAO direction from an LAO direction, the newest frame of the X-ray image data can be used for the left eye. In this case, the past frame of X-ray image data acquired for the duration of a movement of the imaging system 2 to an LAO direction from an RAO direction is inevitably used for the left eye. On the other hand, the past frame of X-ray image data acquired for the duration of a movement of the imaging system 2 to an RAO direction from an LAO direction is inevitably used for the right eye.

The display control as described above can change the display order of X-ray images in synchronized with reversals of the moving direction of the imaging system 2. Then, 3D images which can be stereoscopically viewed can be displayed by sequentially displaying the frames of the X-ray image data after the reordering processing, as frames of displayed image data for left eye and frames of displayed image data for right eye, on the display unit 7.

Note that, images which are not adjacent may be used as a pair of two-parallax images although the adjacent images are used as a pair of two-parallax images in the examples shown in FIG. 3 and FIG. 4. It is experientially suitable for effective stereoscopic viewing that the difference in angle between exposure directions of X-rays exposed in order to acquire two images used as a pair of two-parallax images is set within the range from 1 degree to 3 degrees. Therefore, it is most effective to set the angle difference, between X-ray exposure directions corresponding to a pair of two-parallax images, to 2 degrees.

Accordingly, two frames of X-ray image data, to which the corresponding difference in rotation angle or movement interval of the imaging system 2 becomes a predetermined value, can be used as image data for right eye and image data for left eye. Especially, it is suitable to use two frames of X-ray image data, corresponding to 2 degrees of the difference in rotation angle of the imaging system 2, as image data for right eye and image data for left eye.

In this case, the frame of X-ray image data paired with the newest frame of X-ray image data is not always adjacent and is one acquired with a predetermined difference in rotation angle or movement interval of the imaging system 2. Thereby, two frames of X-ray image data constantly having a predetermined difference in rotation angle, such as 2 degrees, can be displayed for stereoscopic viewing.

By the way, the speed of the imaging system 2 is not constant since the speed becomes zero at the reversing points. That is, the imaging system 2 repeats acceleration and deceleration. Moreover, the imaging system 2 cannot be reciprocated at a constant speed due to mechanical characteristics and control characteristics of the C-shaped arm which constitutes the driving mechanism 10. For this reason, if the control system 3 controls the imaging system 2 so that frames of X-ray image data are acquired with a constant interval, X-rays are intermittently exposed with a temporally constant interval. Consequently, the frames of the X-ray image data are acquired at positions and rotational angles of the imaging system 2 having unequal intervals.

The number of frames of X-ray image data which can be acquired per second is about 30 frames. If frames of X-ray image data are acquired with 30 frames per second, the frames of the X-ray image data are acquired sequentially with the angle difference within about 0.1 to 1 degree. Each frame of the acquired X-ray image data has the exposure angle of X-ray as incidental information. Then, the display processing part 19 can extract two frames of the X-ray image data, between which difference in angle is a constant value, such as 2 degrees, for stereoscopic viewing.

Thereby, it becomes possible to acquire frames of X-ray image data required for stereoscopic viewing without a complicated control of the imaging system 2.

On the other hand, the imaging system 2 is also controllable by the control system 3 so that frames of X-ray image data are acquired with a constant difference in rotational angle or a constant movement interval of the imaging system 2. Specifically, the control system 3 can detect the angle of the imaging system 2 and the C-shaped arm in real time to control the imaging system 2 so that an X-ray is exposed at a predetermined rotational angle difference, such as every 2 degrees.

Such a control of the imaging system 2 makes it possible to acquire frames of X-ray image data required for stereoscopic viewing without acceleration and deceleration of the imaging system 2. Moreover, the exposure of an object O can be reduced since X-ray exposures unnecessary for stereoscopic viewing are not performed. In addition, the extraction processing based on the incidental information of X-ray image data in the display processing part 19 can be omitted.

The above mentioned control method of the imaging system 2 and display method of stereoscopic images can be set up through the interface part 5 shown in FIG. 1. That is, a user can input information for specifying a control method of the imaging system 2 and a display method of stereoscopic images, into the interface part 5 with operation of the input device 6. On the other hand, the interface part 5 is configured to output control information for the imaging system 2 and display processing conditions of stereoscopic images to the control system 3 and the display processing part 19 respectively according to the input specification information.

Next, an operation and an action of the X-ray imaging apparatus 1 will be explained.

First, the interface part 5 displays the setting screen of imaging conditions on the display unit 7. Therefore, a user operates the input device 6 to set up imaging conditions required in order to acquire stereoscopic images of an imaging part of an object O or the like through the setting screen of imaging conditions. At this time, operating conditions of the imaging system 2 including whether the data acquisition is performed with a constant time interval or an equiangular interval, and display conditions of stereoscopic images including a rotational angle difference between two-parallax images are set up.

On the other hand, an object O is set on the top plate of the bed 11. Moreover, a contrast agent is injected into the object O from the contrast medium injector 14, if needed. Then, the start of an imaging is directed to the interface part 5 with an operation of the input device 6. Thereby, the interface part 5 output the control information of the imaging system 2 to the control system 3 according to the operating conditions for the imaging system 2. On the other hand, the interface part 5 gives the display conditions of stereoscopic images to the display processing part 19.

Then, control signals are output from the imaging position control unit 13 of the control system 3 to drive the driving mechanism 7. Thereby, the X-ray exposure part 8 and the X-ray detector 9 reciprocate. On the other hand, a high voltage is applied to the X-ray tube 8A of the X-ray exposure part 8 from the high voltage generator 12 of the control system 3. Thereby, an X-ray is exposed to an imaging part of the object O from the X-ray tube 8A. Then, the X-ray which transmitted the object O is detected by the X-ray detector 9.

Next, an X-ray detection signal is output to the medical image processing apparatus 16 from the X-ray detector 9 through the A/D converter 15. Thereby, the digitized X-ray detection data is acquired in the X-ray image generation part 17. Then, the X-ray image generation part 17 generates X-ray image data by known data processing of the X-ray detection data.

The X-ray image data generated in the X-ray image generation part 17 is given to the X-ray image acquisition part 18. Then, frames of X-ray image data corresponding to at least three X-ray exposure directions are acquired sequentially in the X-ray image acquisition part 18 in the same flow.

Next, the X-ray image acquisition part 18 gives the frames of the X-ray image data to the display processing part 19 sequentially. Then, the display processing part 19 refers to the display conditions of stereoscopic images acquired from the interface part 5. If the frames of the X-ray image data have been acquired with a constant time interval, the newest frame of the X-ray image data and the past frame of the X-ray image data, corresponding to a predetermined angle difference used for the display of stereoscopic images, are specified by the display processing part 19. On the other hand, if the frames of the X-ray image data have been acquired with a constant rotational angle difference, the newest frame of the X-ray image data and the frame of the X-ray image data having the predetermined angle difference from the newest frame of the X-ray image data are specified by the display processing part 19.

Then, the display processing part 19 displays two frames of X-ray image data sequentially on the display unit 7 as the displayed image data for left eye and the displayed image data for right eye. At this time, the display processing part 19 performs the reordering processing of the display order of the two frames of the X-ray image data according to the moving direction of the imaging system 2. Specifically, the display processing part 19 performs the reordering processing that the newest frame of the X-ray image data acquired while the imaging system 2 were moving to an LAO direction from an RAO direction is displayed later as the image data for right eye and the newest frame of the X-ray image data acquired while the imaging system 2 were moving to an RAO direction from an LAO direction is displayed first as the image data for left eye.

Next, the display processing part 19 outputs the image data for left eye and the image data for right eye sequentially to the display unit 7 with a time division. Thereby, a user can stereoscopically view X-ray images displayed on the display unit 7 through the dedicated glasses 20. Specifically, stereoscopic images can be observed as a moving image to which the observing direction changes with time.

That is, the above mentioned X-ray imaging apparatus 1 is an apparatus configured to reciprocate the single imaging system 2 like a pendulum and appropriately reorder frames of X-ray image data acquired in the three or more rotational angles to display them for stereoscopic viewing.

Therefore, according to the X-ray imaging apparatus 1, the reverses in the depth feel due to the turnings of the imaging system 2 can be avoided, and stereoscopic images can be always displayed with a same spatial relationship in the depth direction. Moreover, grasp of stereognostic sense becomes easy since images having a two-parallax are visible with rotation. That is, stereoscopic images to which viewpoint direction changes can be displayed so that stereoscopic viewing from different directions becomes possible.

In addition, frames of X-ray image data are acquired sequentially during movement of the imaging system 2. Therefore, the number of frames of the X-ray image data acquired per unit time can be increased compared with the case where the X-ray image data are acquired with stopping the imaging system 2. As a result, a real time display becomes possible. Moreover, in case of injecting a contrast agent, more X-ray contrast images can be acquired. That is, a contrast period can be used effectively for acquisition of X-ray image data.

Moreover, according to the X-ray imaging apparatus 1, stereoscopic images can be generated and displayed by using the single imaging system 2. In addition, the X-ray imaging apparatus 1 does not need complicate image reconstruction processing for generating and displaying stereoscopic images. Therefore, stereoscopic images can be generated and displayed by a very cheap and simple composition and data processing. In other words, even the X-ray imaging apparatus 1 having the single imaging system 2 can generate and display stereoscopic images which are not inferior to those which can be generated in an X-ray imaging apparatus having plural imaging systems or an X-ray imaging apparatus performing advanced image reconstruction processing.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, although a case where two-parallax images for a 3D image allowing stereoscopic viewing are acquired by using the X-ray imaging apparatus having the single imaging system has been explained in the above-mentioned example, similar two-parallax images can be also acquired in an X-ray imaging apparatus having plural imaging systems by using one of the plural imaging systems. That is, two-parallax images for a 3D image can be acquired by using an X-ray imaging apparatus which acquires X-ray image data of an object using at least one imaging system.

Moreover, although an example case where the X-ray imaging apparatus is for circulatory organs has been explained in the above-mentioned example, similar imaging and display of a stereoscopic image with reordering of a display order are also possible in another type of X-ray imaging apparatus. In X-ray imaging apparatuses, the exposure direction of an X-ray and the coordinate systems commonly used to specify the exposure direction of the X-ray differ depending on an intended use.

Figure 5A:
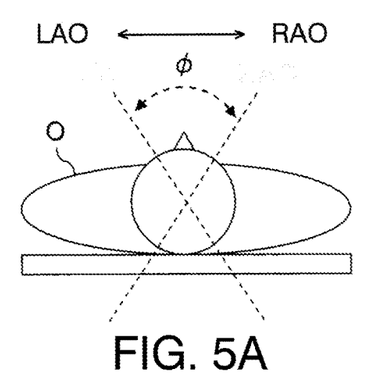
FIGS. 5A and 5B show the coordinate system used for specifying the exposure direction of X-ray in an X-ray imaging apparatus for circulatory organ.
Figure 5B:
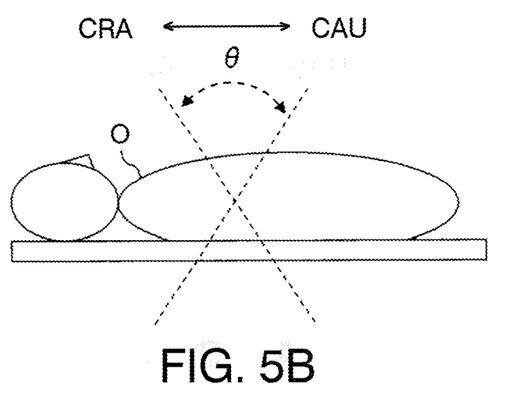

FIGS. 5A and 5B show the coordinate system used for specifying the exposure direction of X-ray in an X-ray imaging apparatus for circulatory organs.

Although a configuration of the general X-ray imaging apparatus 1 is shown in FIG. 1, an X-ray imaging apparatus for circulatory organs, which mainly aims at imaging of blood vessels, has the X-ray tube 8A below the object O and the X-ray detector 9 above the object O in an usual state. Therefore, the exposure direction of an X-ray is defined by the first angle φ between the LAO direction and the RAO direction of the object O shown in FIG. 5A and also the second angle θ between the cranial (CRA) direction and the caudal (CAU) direction of the object O shown in FIG. 5B. In this case, the newest frame of an X-ray image becomes an image for right eye when the imaging system 2 moves to the LAO direction from the RAO direction as mentioned above.

Figure 6:
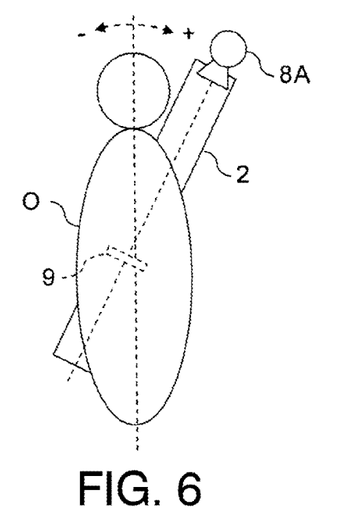
FIG. 6 shows the coordinate system used for specifying the exposure direction of X-ray in an X-ray imaging apparatus for breast.

FIG. 6 shows the coordinate system used for specifying the exposure direction of X-ray in an X-ray imaging apparatus for breast.

On the other hand, an X-ray imaging apparatus for breasts used as a mammography apparatus has the X-ray tube 8A above the object O and the X-ray detector 9 below the object O in an usual state. Thus, in the X-ray imaging apparatus for breasts, an imaging angle is defined by the plus direction and the minus direction from the center position on the rotational plane of the imaging system 2 as shown in FIG. 6.

Figure 7A:
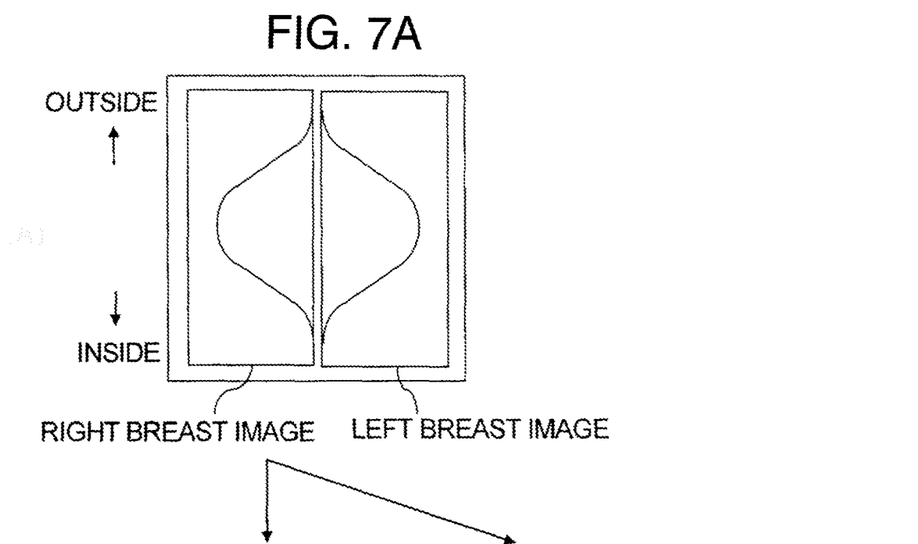
FIGS. 7A and 7B show an example of directions of X-ray images acquired by an X-ray imaging apparatus for breast and display directions of the X-ray images for stereoscopic viewing.
Figure 7B:
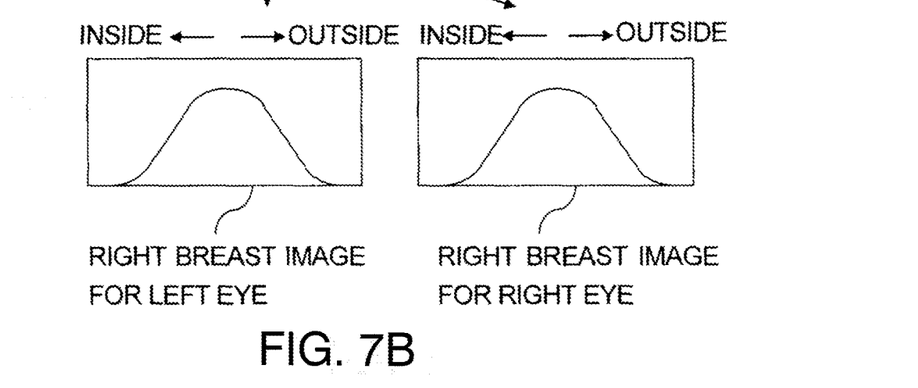

FIGS. 7A and 7B show an example of directions of X-ray images acquired by an X-ray imaging apparatus for breast and display directions of the X-ray images for stereoscopic viewing.

As shown in FIG. 7A, the X-ray image data in which the right breast of the object O is depicted and X-ray image data in which the left breast of the object O is depicted are acquired repeatedly in the X-ray imaging apparatus for breasts. When stereoscopic viewing is not performed, each acquired X-ray image is generally displayed on the display unit in the direction that the inside of the breast becomes the lower part and the outside of the breast becomes the upper part as shown in FIG. 7A.

Therefore, in case of displaying a stereoscopic viewing image, it is necessary to display two frames of X-ray images, having two parallaxes, in which the right breasts are depicted, for the left and right eyes as shown in FIG. 7B or two frames of X-ray images, having two parallaxes, for left and right eyes, in which the left breasts are depicted.

Then, the display processing part 19 can perform extraction processing of two frames of X-ray image data in which the left breasts of the object O are depicted or the right breasts of the object O are depicted. Thus, the display processing part 19 can generate image data for displaying the respective X-ray images for the left and right eyes in a suitable direction for the stereoscopic viewing as shown in FIG. 7B by rotation processing according to the imaging direction of the extracted two frames of the X-ray image data. Note that, in the example shown in FIG. 7B, the X-ray image for the left eye and the X-ray image for the right eye in which the right breasts have been depicted are displayed in a same direction in which the inside becomes the left side and the outside becomes the right side.

In case of the X-ray imaging apparatus for breasts which performs a display as shown in FIG. 7B, the newest frame of an X-ray image becomes an image for right eye when the imaging system moves to the plus side from the minus side.

Figure 8:
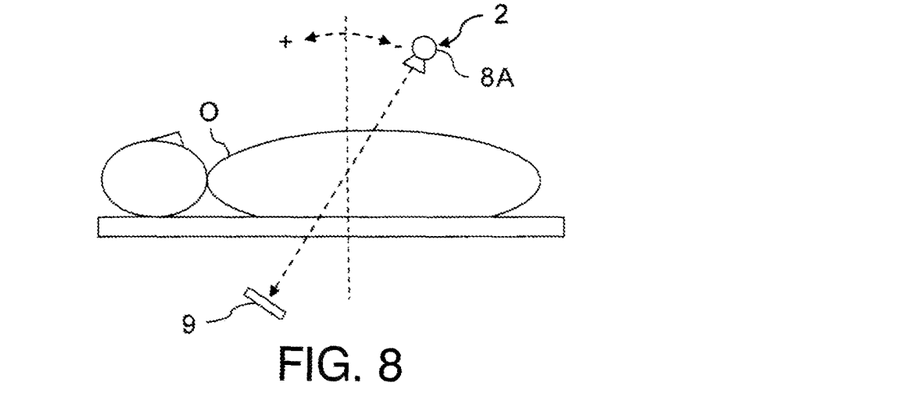
FIG. 8 shows the coordinate system used for specifying the exposure direction of X-ray in a general X-ray imaging apparatus.

FIG. 8 shows the coordinate system used for specifying the exposure direction of X-ray in a general X-ray imaging apparatus.

A general X-ray imaging apparatus for imaging various imaging targets has the X-ray tube 8A above the object O and the X-ray detector 9 under the object O in an usual state. Then, an imaging angle is defined by the plus direction and the minus direction from the center position on the rotational plane of the imaging system 2 as shown in FIG. 8.

Figure 9A:
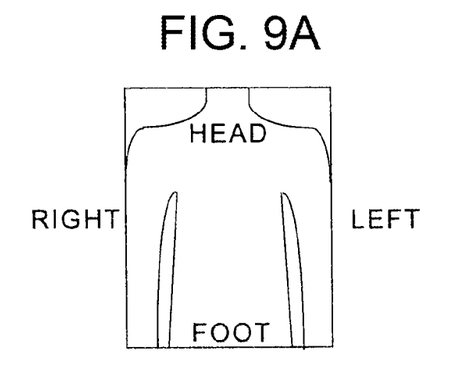
FIGS. 9A and 9B show an example of a direction of an X-ray image acquired by a general X-ray imaging apparatus and display directions of the X-ray images for stereoscopic viewing.
Figure 9B:
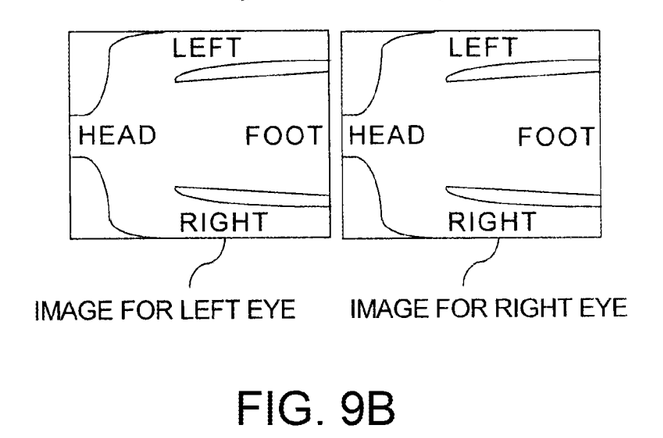

FIGS. 9A and 9B show an example of a direction of an X-ray image acquired by a general X-ray imaging apparatus and display directions of the X-ray images for stereoscopic viewing.

An X-ray image acquired by a general X-ray imaging apparatus is displayed in a direction in which the head lies the upside of the image, the right hand side lies the left side of the image, the left hand side lies the right side of the image, and the tail part lies the downside of the image as shown in FIG. 9A. That is, an X-ray image is displayed in a direction so that a human body is seen from the front.

Then, X-ray image data may be displayed with a rotation, so that the moving direction of the imaging system becomes the right and left direction, for displaying a stereoscopic viewing image. That is, in case of rotating the imaging system in the craniocaudal direction of the object O, the respective X-ray images for the left and right eyes can be displayed with a rotation so that the craniocaudal direction becomes the right and left direction, as shown in FIG. 9B. That is, display processing to generate image data for the left and right eyes can be performed with rotating frames of X-ray image data so that the craniocaudal direction of the object O becomes the right and left direction, in the display processing part 19. In this case, the newest frame of X-ray image becomes an image for the right eye when the imaging system moves to the minus side from the plus side.

As mentioned above, the reciprocating direction of the imaging system 2 is determined according to the imaging purpose. Therefore, the display processing part 19 have only to be configured to use the newest frame of X-ray image data, acquired while the imaging system 2 moves in the first direction, as image data for the right eye and to use the newest frame of X-ray image data, acquired while the imaging system 2 moves in the second direction which is opposite to the first direction, as image data for the left eye. That is, the newest frame of X-ray image data can be used as image data for the right eye when the newest frame of the X-ray image data is acquired while the imaging system 2 moves in the first direction. On the other hand, the newest frame of X-ray image data can be used as image data for the left eye when the newest frame of the X-ray image data is acquired while the imaging system 2 moves in the second direction which is opposite to the first direction. Then, the first direction and the second direction can be determined according to the use of the X-ray imaging apparatus.

Moreover, depending on the use of the X-ray imaging apparatus, the display processing part 19 may perform coordinate conversion processing of X-ray image data for a display with a rotation or a reverse to use the X-ray image data after the coordinate conversion as image data for stereoscopic viewing. That is, image data which can be stereoscopically viewed can be generated by coordinate conversion of frames of X-ray image data according to the moving direction of the imaging system 2.

Figure 10A:
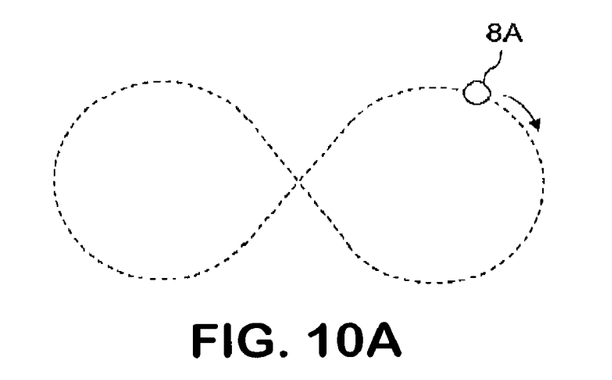
FIGS. 10A and 10B illustrate examples of movement of an X-ray tube along a figure-eight locus and an ellipse, respectively.
Figure 10B:
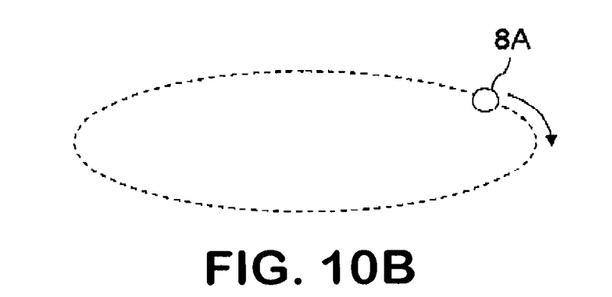

Furthermore, although the above-mentioned example explains the case where the control system 3 moves the imaging system 2 along with a locus of a pendulum on a plane, it is also possible to move the imaging system 2 so that a locus of the imaging system 2 becomes one of a pendulum when the locus of the imaging system 2 is projected on a plane. As a specific example, the imaging system 2 can be moved along with a locus having a shape of an ellipse or a character of eight. In this case, a high-speed imaging is attained since the imaging system 2 does not stand still.

What is claimed is:

1. An X-ray imaging apparatus, comprising:
   an imaging system, having an X-ray tube and an X-ray detector, configured to acquire X-ray image data of an object by using at least one imaging system;
   a control system configured to control the imaging system to acquire frames of the X-ray image data corresponding to mutually different not less than three directions by reciprocating the imaging system; and
   a display processing circuit configured to generate stereoscopically visible image data by lining up the frames of the X-ray image data in a display order different from an acquisition order of the frames of the X-ray image data, the display order being determined according to whether a moving direction of the imaging system is clockwise or counterclockwise as viewed from a craniocaudal direction of the object, the display order being along an increasing time direction, the frames of the X-ray image data being acquired during a movement of the imaging system and corresponding to positions that are between but not including ends of a movement range of the imaging system.

2. The X-ray imaging apparatus of claim 1,
   wherein said display processing circuit is configured to use a newest frame of the X-ray image data as image data for a right eye when the newest frame of the X-ray image data was acquired while the imaging system moves in a first direction, and use the newest frame of the X-ray image data as image data for a left eye when the newest frame of the X-ray image data was acquired while the imaging system moves in a second direction opposite to the first direction.

3. The X-ray imaging apparatus of claim 1,
   wherein said display processing circuit is configured to use a newest frame of the X-ray image data as image data for a right eye when the newest frame of the X-ray image data was acquired while the imaging system rotates toward a left anterior oblique direction, and use the newest frame of the X-ray image data as image data for a left eye when the newest frame of the X-ray image data was acquired while the imaging system rotates toward a right anterior oblique direction, a rotation axis of the imaging system being directed to the craniocaudal direction of the object.

4. The X-ray imaging apparatus of claim 3,
   wherein the imaging system is configured to acquire the X-ray image data by exposing an X-ray in an exposure direction defined by a first angle between a left anterior oblique direction and a right anterior oblique direction of the object, and a second angle between a first direction toward a cranial direction and a second direction toward a caudal direction of the object.

5. The X-ray imaging apparatus of claim 1,
   wherein said display processing circuit is configured to use two frames of the X-ray image data as image data for a right eye and image data for a left eye, a movement interval or a difference in a rotation angle of the imaging system corresponding to the two frames of the X-ray image data being a predetermined value.

6. The X-ray imaging apparatus of claim 5,
   wherein said control system is configured to control the imaging system to acquire the frames of the X-ray image data with the movement interval or the difference in the rotation angle of the imaging system.

7. The X-ray imaging apparatus of claim 5, wherein said control system is configured to control the imaging system to acquire the frames of the X-ray image data with a constant time interval.

8. The X-ray imaging apparatus of claim 1, wherein said display processing circuit is configured to generate the stereoscopically visible image data by a coordinate conversion of the frames of the X-ray image data, the coordinate conversion corresponding to a moving direction of the imaging system.

9. The X-ray imaging apparatus of claim 8, wherein the imaging system is configured to repeatedly acquire X-ray image data in which a right breast of the object is depicted and X-ray image data in which a left breast of the object is depicted; and
the display processing circuit is configured to generate image data for a right eye and image data for a left eye to be displayed in a direction for a stereoscopic viewing by rotating two frames of the X-ray image data each depicting the left breast of the object or two frames of the X-ray image data each depicting the right breast of the object.

10. The X-ray imaging apparatus of claim 8, wherein the imaging system is configured to acquire the X-ray image data in a craniocaudal direction of the object; and
the display processing circuit is configured to generate image data for a right eye and image data for a left eye by rotating the frames of the X-ray image data to make the craniocaudal direction be a right and left direction.

11. The X-ray imaging apparatus of claim 1, wherein said control system is configured to move the imaging system along an ellipse or figure-eight locus, a projection of the locus on a plane becoming pendular.

12. The X-ray imaging apparatus of claim 1, wherein a difference in angle between exposure directions of X-rays exposed in order to acquire two-parallax images consisting of the stereoscopically visible image data generated by the display processing circuit is set within a range from 1 degree to 3 degrees.

13. The X-ray imaging apparatus of claim 1, wherein the frames of the X-ray image data are acquired with a constant time interval by the imaging system of which speed is not constant.

14. The X-ray imaging apparatus of claim 1, wherein the frames of the X-ray image data are acquired with a constant difference in rotational angle of the imaging system of which speed is not constant.

15. A medical image processing apparatus, comprising:
an image acquisition circuit configured to acquire frames of X-ray image data corresponding to mutually different not less than three directions, the frames of the X-ray image data being acquired by reciprocating a single imaging system, the frames of the X-ray image data being acquired during a movement of the imaging system and corresponding to positions that are between but not including ends of a movement range of the imaging system; and
a display processing circuit configured to generate stereoscopically visible image data by lining up the frames of the X-ray image data in a display order different from an acquisition order of the frames of the X-ray image data, the display order being determined according to whether a moving direction of the imaging system is clockwise or counterclockwise as viewed from a craniocaudal direction of the object, the display order being along an increasing time direction.

16. An X-ray imaging method, comprising:
acquiring X-ray image data of an object by using an imaging system;
controlling the imaging system to acquire frames of the X-ray image data corresponding to mutually different not less than three directions by reciprocating the imaging system, the frames of the X-ray image data being acquired during a movement of the imaging system and corresponding to positions that are between but not including ends of a movement range of the imaging system; and
generating stereoscopically visible image data by lining up the frames of the X-ray image data in a display order different from an acquisition order of the frames of the X-ray image data, the display order being determined according to whether a moving direction of the imaging system is clockwise or counterclockwise as viewed from a craniocaudal direction of the object, the display order being along an increasing time direction.

17. A medical image processing method, comprising:
acquiring frames of X-ray image data corresponding to mutually different not less than three directions, the frames of the X-ray image data being acquired by reciprocating a single imaging system, the frames of the X-ray image data being acquired during a movement of the imaging system and corresponding to positions that are between but not including ends of a movement range of the imaging system; and
generating stereoscopically visible image data by lining up the frames of the X-ray image data in a display order different from an acquisition order of the frames of the X-ray image data, the display order being determined according to whether a moving direction of the imaging system is clockwise or counterclockwise as viewed from a craniocaudal direction of the object, the display order being along an increasing time direction.

* * * * *